(12) United States Patent
Fesmire et al.

(10) Patent No.: US 6,824,306 B1
(45) Date of Patent: Nov. 30, 2004

(54) THERMAL INSULATION TESTING METHOD AND APPARATUS

(75) Inventors: James E. Fesmire, Titusville, FL (US); Stanislaw D. Augustynowicz, Titusville, FL (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 10/318,665

(22) Filed: Dec. 11, 2002

(51) Int. Cl.[7] .............................................. G01N 25/20
(52) U.S. Cl. ..................................... 374/43; 374/34
(58) Field of Search ............................ 374/43, 44, 30, 374/33, 34, 51, 29, 31, 32; 422/51; 436/147, 149, 151; 62/51.1

(56) References Cited

U.S. PATENT DOCUMENTS

| | | | | |
|---|---|---|---|---|
| 2,699,060 A | * | 1/1955 | Safford | 374/51 |
| 3,242,716 A | * | 3/1966 | Glaser et al. | 374/44 |
| 3,263,485 A | * | 8/1966 | Mahmoodi | 374/44 |
| 3,266,290 A | * | 8/1966 | Gottfried | 374/44 |
| 3,705,498 A | * | 12/1972 | DeHaan | 62/47.1 |
| 4,187,956 A | * | 2/1980 | Schrawer et al. | 220/745 |
| 4,302,943 A | * | 12/1981 | Niemann et al. | 374/40 |
| 4,350,017 A | * | 9/1982 | Kneip et al. | 62/48.1 |
| 4,393,716 A | * | 7/1983 | Clark et al. | 374/51 |
| 4,522,512 A | | 6/1985 | Atkins | 374/44 |
| 4,963,499 A | * | 10/1990 | Stockton et al. | 436/147 |
| 5,193,909 A | | 3/1993 | Duncan | 374/29 |
| 5,246,759 A | * | 9/1993 | Keller | 428/74 |
| 5,386,706 A | | 2/1995 | Bergsten et al. | 62/45.1 |
| 5,620,253 A | | 4/1997 | Graebner et al. | 374/43 |
| 5,708,069 A | * | 1/1998 | Burns et al. | 524/403 |
| 5,749,537 A | * | 5/1998 | Muzio et al. | 242/439.5 |
| 5,806,979 A | | 9/1998 | Gschneidner, Jr. et al. | 374/34 |

(List continued on next page.)

OTHER PUBLICATIONS

"Standard Test Method for Heat Flux Through Evacuated Insulations Using a Guarded Flat Plate Boiloff Calorimeter," C745–92 (1999), American Society for Testing and Materials, 1999 (8 pages).*

(List continued on next page.)

*Primary Examiner*—Diego Gutierrez
*Assistant Examiner*—Stanley J. Pruchnic, Jr.
(74) *Attorney, Agent, or Firm*—Randall M. Heald; Gary Borda; Guy Miller

(57) ABSTRACT

A test apparatus and method of its use for evaluating various performance aspects of a test specimen is disclosed. A chamber within a housing contains a cold mass tank with a contact surface in contact with a first surface of a test specimen. The first surface of the test specimen is spaced from the second surface of the test specimen by a thickness. The second surface of the test specimen is maintained at a desired warm temperature. The first surface is maintained at a constant temperature by a liquid disposed within the cold mass tank. A boil-off flow rate of the gas is monitored and provided to a processor along with the temperature of the first and second surfaces of the test specimen. The processor calculates thermal insulation values of the test specimen including comparative values for heat flux and apparent thermal conductivity (k-value). The test specimen may be placed in any vacuum pressure level ranging from about 0.01 millitorr to 1,000,000 millitorr with different residual gases as desired. The test specimen may be placed under a mechanical load with the cold mass tank and another factors may be imposed upon the test specimen so as to simulate the actual use conditions.

22 Claims, 2 Drawing Sheets

U.S. PATENT DOCUMENTS

| | | | | |
|---|---|---|---|---|
| 5,940,784 A | * | 8/1999 | El-Husayni | 374/43 |
| 5,997,174 A | | 12/1999 | Wyland | 374/43 |
| 6,039,471 A | | 3/2000 | Wyland | 374/43 |
| 6,095,680 A | | 8/2000 | Baratta | 374/43 |
| 6,142,662 A | | 11/2000 | Narh et al. | 374/44 |
| 6,273,604 B1 | | 8/2001 | Hemmerich et al. | 374/45 |
| 6,487,866 B1 | * | 12/2002 | Fesmire et al. | 374/44 |
| 6,742,926 B1 | * | 6/2004 | Fesmire et al. | 374/43 |
| 2003/0072349 A1 | * | 4/2003 | Osone et al. | 374/43 |

OTHER PUBLICATIONS

Bapat, S. L., et al., "Experimental investigations of multi-layer insulation,", Cryogenics (UK) vol. 30,, No. 8 Aug. 1990, pp. 711–719.*

* cited by examiner

THERMAL INSULATION TESTING METHOD AND APPARATUS

ORIGIN OF THE INVENTION

This invention was made in the performance of work under a NASA contract and by an employee of the United States Government and is subject to the provisions of Public Law 96-517 (35 U.S.C. §202) and may be manufactured and used by or for the Government for governmental purposes without the payment of any royalties thereon or thereof. In accordance with 35 U.S.C. §202, the contractor elected not to retain title.

BACKGROUND OF THE INVENTION

1. Field of the Invention

This invention relates to a test apparatus and a method of making precise thermal performance measurements of thermal insulation specimens, and more specifically to a comparative testing method and apparatus for evaluating thermal insulation materials and composite systems in flat plate configurations for low temperature applications.

2. Relevant Art

U.S. Pat. No. 3,242,716 is directed to a method and apparatus for testing thermal conductivity of insulation placed over a test apparatus. This device employs separate passageways for introducing a cryogenic fluid into the test chamber and disposing of the boiled-off gases. The method of testing is consistent with a boil off calorimeter, i.e., the absolute method as set forth in ASTM procedure C745. To perform the testing procedure according to the invention, an extended amount of time of carefully controlled monitoring may be necessary to complete the test. In comparison, the present invention follows the "comparative method" including controlled parasitic heat leak in which no monitoring of the testing process is required. Once the testing process is initiated, it will continue without the need for intervention until the cryogenic liquid is completely boiled-off, allowing for precise measurement of the thermal properties of the insulation material.

U.S. Pat. No. 4,396,300 is directed to a test apparatus for testing the heat transfer and friction characteristics of a tube. It does not teach how to test a flat thermal insulation specimen.

Precise measurement of thermal performance of a thermal insulation system is advantageous in many applications. As technology advances, the use of cryogenics has become more and more commonplace. As an example, hydrogen may become the common fuel source. An infrastructure for the storage, distribution and handling of liquid hydrogen would then be needed for many applications. This demand for the storage and handling of various cryogens will require the development of highly effective thermal insulation systems.

At least three ASTM procedures exist for testing thermal properties flat slab specimens: C177 (absolute method, guarded hot plate), C518 (comparative method, heat flow meter), and C745 (absolute method, boil off calorimeter). C177 is difficult to apply for a large temperature differential (high delta T) and in vacuum conditions. The document summary provided by ASTM for this procedure specifically warns that special precautions are required for conducting the test under vacuum conditions. C518 is used mostly for near ambient temperature testing of materials such as building insulation and requires the measurement of specimens of well known thermal transmission properties to calibrate the apparatus. C745 is very difficult in set-up and execution in part because of the necessity of providing a cryogenic guard vessel. These methods are typically limited to small temperature differences (such as 20K) and a limited range of vacuum pressure.

One valuable technique for testing the thermal performance of materials, preferably insulation material, is boil-off testing. Boil-off testing is accomplished by filling a vessel with a fluid that boils, or evaporates, below ambient temperature. Cryogens such as liquid nitrogen, liquid helium, liquid methane, liquid hydrogen, or other known refrigerants may be used. The vessel is placed on top of the testing material. The vessel (cold mass tank) is then filled with the cryogenic liquid. A calorimetry method is then used to determine the thermal conductivity of the testing material by determining the amount of heat that passes through the test material to the vessel containing cryogenic liquid. The cryogenic liquid boil-off rate from the vessel is directly proportional to the heat leak rate passing through the test material to the cryogenic liquid in the vessel. For a test material under a set vacuum pressure, the apparent thermal conductivity (k-value) is determined by measuring the flow rate of cryogenic boil-off gas at given warm and cold boundary temperatures across the thickness of the sample.

Although known cryogenic boil-off techniques and devices have been utilized to determine the thermal conductivity of insulation material, the previous techniques and devices have proven less than successful for a variety of reasons. First, few such cryogenic devices are in operation because of their impracticality from an engineering point of view. Previous cryogenic boil-off devices made it extremely difficult to obtain accurate, stable thermal measurements and required extremely long set up times. Prior testing devices also needed highly skilled personnel that could oversee the operation of the cryogen testing device for extended periods of time, often exceeding 24 hours to many days in some cases. Additionally, constant attention was required to operate previous cryogenic testing devices to make the necessary fine adjustments required of the testing apparatus. Second, the testing of high performance materials such a multilayer insulation requires extreme care during installation. Inconsistency in performing installation techniques is a dominant source of error and poses a basic problem in the comparison of such materials. Localized compression effects, sensor installation, and out-gassing provided further complications. Third, measurements of various testing parameters were not carefully determined or controlled in known testing devices. Measurement of temperature profiles for insulation material was either not done or was minimal because of the practical difficulties associated with the placement, feed-though, and calibration of the temperature sensors. Vacuum levels were restricted to one or two set points or not actively controlled altogether. Fourth, previous cryogenic testing devices required complex thermal guards having cryogenic fluid filled chambers to reduce unwanted heat leaks (end effects) to a tolerable level. The previous technique for providing thermal guards, i.e., filling guard chambers with the cryogen, caused much complexity both in construction and operation of the apparatus. Known techniques added the further complication of heat transfer between the test chamber and the guard chambers due to thermal stratification of the liquid within the chambers.

Accordingly, there exists a need for a method, preferably as simple as possible, for evaluating the thermal performance of materials under actual use conditions. These conditions include large temperature differences (as much as 200K) and a full range of vacuum pressure levels (between approximately $1 \times 10^{-5}$ torr to approximately 1000 torr).

SUMMARY OF THE INVENTION

Consequently, it is a primary object of the present invention to provide a method and apparatus for obtaining data to measure the heat leak rate through materials under actual use conditions such as temperature, vacuum, environment, and/or mechanical loading.

It is a further object of the present invention to provide a method and apparatus for providing comparative heat leak rates and comparative apparent thermal conductivity values.

Another object of the present invention is to provide a method and apparatus which is easily employed to provide the thermal performance of actual specimens.

Accordingly, the present invention provides a test apparatus and method to measure the heat leak rate through materials.

To eliminate or minimize the foregoing and other problems, a new system and method of testing thermal insulation systems has been developed. In particular, the present invention overcomes the foregoing problems by providing a cryogenic testing apparatus having a boil-off calorimeter system for calibrated measurement of the apparent thermal conductivity (k-value) of a testing material, preferably insulation material, at a fixed vacuum level. Vacuum levels can range from high vacuum (below $1 \times 10^{-5}$ torr) to soft vacuum (about 1 to 10 torr) to no vacuum (above 760 torr).

The test apparatus is preferably comprised of a test assembly having a single liquid nitrogen feed through assembly to fill liquid nitrogen into a cavity formed in a cold mass tank and subsequently vent nitrogen gas as it boils-off of the liquid nitrogen present in the cold mass tank cavity. The cold mass tank cavity receives cryogenic liquid from the feed through assembly wherein the cryogenic liquid contacts a side of the cold mass tank having contact surface directly contacting a test specimen mounted in the test apparatus. The cold mass tank and the test specimen are preferably contained within a vacuum chamber. Compressions rods may be utilized to press the cold mass tank into contact with the test specimen, providing a measurable mechanical loading to the test specimen, thereby controlling the thickness of the test specimen. Insulation and shield guards may surround the test specimen to reduce the at transfer from the sides of the test specimen to minimal and repeat able levels.

A heater may be used to apply a desired temperature on a first or heated side of the test specimen while the cold mass eventually achieves and maintains a steady state temperature, for example about 80K, on the cold or second side of the test specimen. The heat transfer through the test specimen boils off, or evaporates, the liquid nitrogen in the cold mass tank that can be measured by a mass flow meter. When the boil-off is complete and stability is reached, the thermal conductivity of the test specimen may be calculated from temperature and mass flow rate data. The vacuum environment may be established along with the mechanical loading and charts showing the thermal performance of the test specimen under loading and various vacuum conditions may be created for future use.

BRIEF DESCRIPTION OF THE DRAWINGS

The particular features and advantages of the invention as well as other objects will become apparent from the following description taken in connection with the accompanying drawing in which.

DETAILED DESCRIPTION OF THE PREFERRED EMBODIMENT

Figure 1:
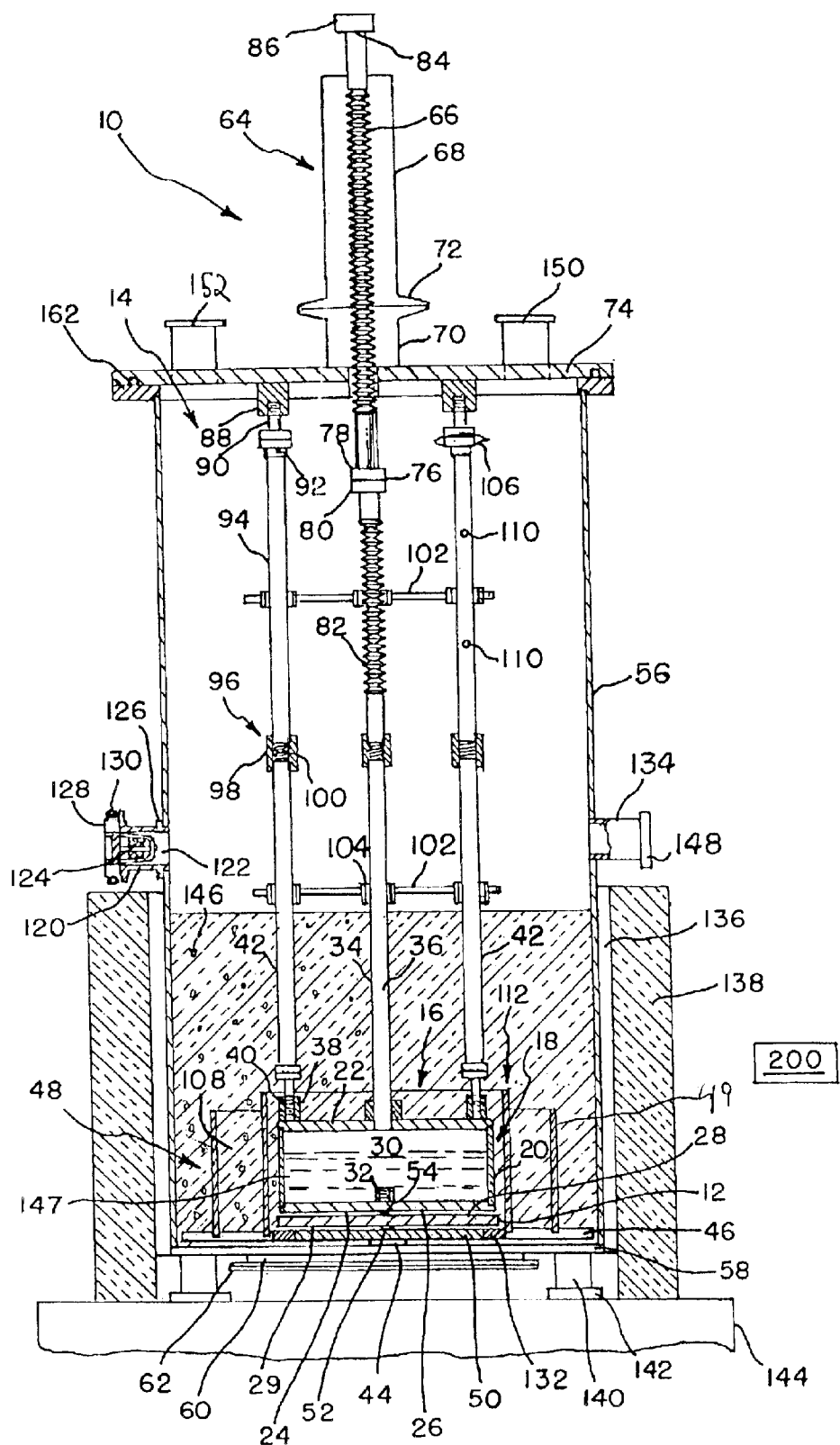
FIG. 1 depicts a cross sectional side view of a test assembly constructed in accordance with the preferred embodiment of the present invention.

Referring to FIG. 1, a test apparatus is illustrated at 10. The test apparatus 10 is adaptable to test the thermal performance characteristics of a test specimen 12 so that designers and/or builders may accurately predict the heat losses in a similarly-shaped specimen.

Test specimen 12 may be formed of insulation material such as foams, powders, blankets, multilayer insulation systems, composite panels, and other materials or combinations of materials. Of course other materials and configurations as well coatings, biological substances, structural materials, etc., whether rigid or deformable could also be utilized as test specimens 12.

Test apparatus 10 may be used for determining various thermal performance characteristics such as the heat transfer rate (Q), the heat flux rate (q), and the apparent thermal conductivity (k-value), and/or the insulating effectiveness value (R) of a test specimen 12.

A test apparatus no formed in accordance with a preferred embodiment of the present invention has a vacuum chamber 14 enclosing a cold mass tank 16. The cold mass tank 16 is preferably comprised of a substantively hollow cylinder 18 enclosed at each end and formed by rolling a ring 20 about top and bottom disks 22 and 24. The bottom disk 24 provides contact surface 26 for contacting a first or top surface 28 of a typical test specimen 12. The bottom surface 29 of the test specimen 12 is spaced by a known/or measurable thickness from its top surface 28.

Figure 3:
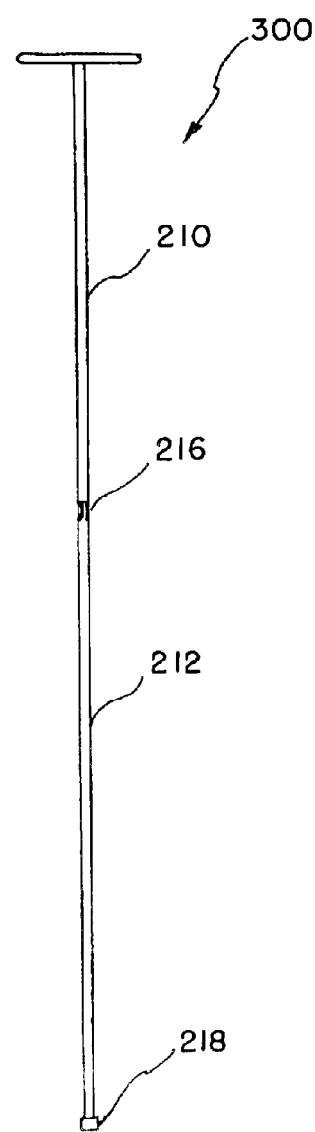
FIG. 3 depicts a cold mass handling tool formed in accordance with a preferred embodiment of the present invention.

The cold mass tank 16 includes a cavity 30. and, extending within a portion of cavity 30, a receiver 32 which may take the form of a nut adaptable for receiving a threaded cold mass handling tool 300 (shown in FIG. 3). An end of tool 300 includes an inner vessel threaded attachment member 218 that can be aligned with and screwed into the receiver 32 in order to position the cold mass tank 16 at a desired location within vacuum chamber 14. A tube 34 extends from the top disk 22 and provides fluid communication through an interior bore 36 into the cavity 30 within cold mass tank 16. This allows for passage of the cold mass handling tool 300 into the cold mass tank 16 as well for the ability to fill and vent the cold mass tank cavity 30 with a liquid fluid such as a cryogenic liquid nitrogen as will be explained in further detail below. The tube 34 is preferably welded into the top disk 22.

The cold mass handling tool 300 facilitates removal of the cold mass tank 16 from the vacuum chamber 14. In particular, specialized tool 300 has a T-shaped handle portion 210 and a handling tool portion 212. The T-shaped handle portion 210 attaches to the handling tool portion 212 at a threaded screw connection 216. The handling tool portion 212 also includes the inner vessel attachment 218 disposed at the end of tool 300 for attachment to receiver 32 of cold mass tank 16 as discussed above.

The cold mass tank 16 is also equipped with bosses 38 that contain threaded bores 40 therein. The bosses 38 are adapted to receive compression rods 42 which may be utilized to exert a desired mechanical force upon cold mass tank 16, resulting in a change of pressure between contact surface 26 and test specimen 12. By twisting the rods 42 relative to the bosses 38, the position of the cold mass tank 16, and the resulting contact force, may be pre-selected. In the same manner, the desired test thickness for a specific test specimen 12 can be achieved. A load cell 44 may be utilized to measure the compression placed upon the test specimen 12 by the compression rods 42 acting through cold mass tank 16. Load cell 44 may be located between a plate assembly 46 which is preferably substantially isothermal and a bottom surface 58 of a housing 56 defined by vacuum chamber 14. The isothermal plate assembly 46 is preferably grooved to accept an outer guard ring 48, a copper disk 50, and the test specimen 12 itself, as will be explained in more detail below.

The copper disk 50 is preferably located in the center of the isothermal plate assembly 46. A first temperature sensor 52 is preferably located on top of copper disk 50 in order to measure the warm boundary temperature near the bottom surface 29 of test specimen 12. A second temperature sensor 54 is preferably located on the top surface 28 of the test specimen 12 to measure the cold boundary temperature near the bottom surface 26 of the cold mass tank 16. These temperature data are provided to a processor 200. The copper disk 50 and the cold mass tank contact surface 26 are preferably of the same or similar configuration and have a diameter which has a ratio of about 3:4 to the diameter of the test specimen 12.

Disk 50 is preferably made of copper to ensure the surface flatness substantially matches the bottom of the vacuum chamber 14 and/or load cell 44 as well as to direct the heat flow substantially in the axial direction through test specimen 12. When forming the isothermal plate assembly 46, it is preferable to remove any sharp edges to provide for convenient centering and fit-up of the test specimen 12 upon installation.

The bottom surface 58 of vacuum chamber 14 is preferably located below the load cell 44, if utilized, and the isothermal plate assembly 46. A heater 60 separate from vacuum chamber 14 is preferably positioned below bottom surface 58. and a fire blanket 62, preferably in multiple layers, may be located below heater 60 to reflect heat backup towards the test specimen 12 as well as to provide a safety barrier while conducting the tests in the vacuum chamber 14. Further insulation wraps 138 may be positioned about the exterior of the vacuum chamber 14 to provide test apparatus 10 with additional thermal stability to negate effects of varying room environmental conditions.

In order to fill the cold mass tank cavity 30 with the cryogenic liquid nitrogen, a feed-through assembly 64 is utilized. Feed through assembly 64 preferably includes a thin-walled, hollow bellows 66 contained within a barrel 68 that is connected to an extension 70 at plan 72. Bellows 66 passes through a top 74 of vacuum chamber 14 and connects to a fitting assembly 76. In the preferred embodiment, a female nut 78 forms the upper portion of fitting assembly 76 while a copper gasket retainer 80 forms the lower portion of fitting assembly 76. A second, thin-wall bellows 82 connects with tube 34 as illustrated in FIG. 1. Accordingly, the bore 36 communicates through the tube 34, the hollow bellows passageways 82, 66 and an outlet port 84, where it joins a flow meter 86, the operation of which will be explained. The funnel or cold mass fill tube assembly 15 shown in FIG. 2, may be used to cool, fill, and vent liquid or gaseous nitrogen to or from the cold mass tank 16 through the single, common outlet port 84. The thin-wall bellows 66 and 82, with an equivalent heat transfer length of about four times the installed length, are employed to minimize the solid conduction heat leak to the cold mass tank 16 and its cavity 30.

Figure 2:
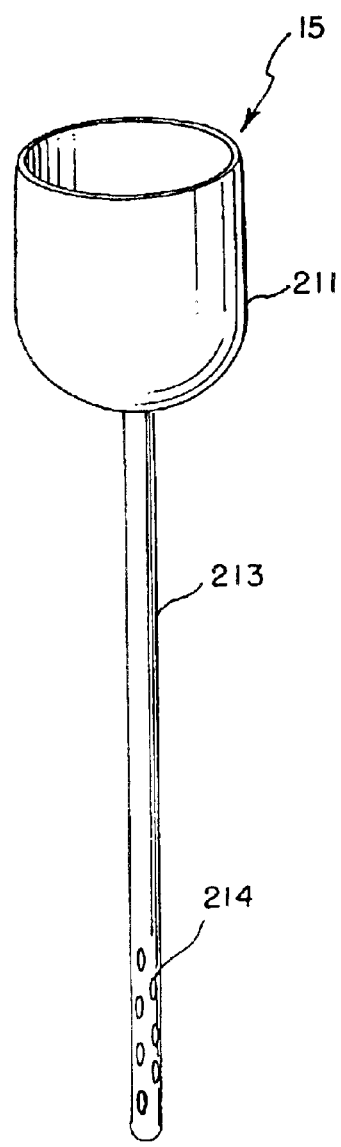
FIG. 2 depicts a fluid fill assembly for use in filling the cold mass tank shown in FIG. 1.

The funnel and fill tube assembly 15, as shown in FIG. 2, includes a large fluid receiving substantially cylindrically-shaped portion 211 in fluid communication with an elongated tubular portion 213 adaptable for extending through the bore 36 to the bottom of cold mass tank 16. A series of small openings 214 extend through lower wall portions of tubular portion 213, allowing cryogen liquid nitrogen to flow from cylindrical portion 211, through tubular portion 213 and exit via openings 214 into the cold mass tank cavity 30. The tubular portion 213 has a smaller outer diameter than the inside diameter of bore 36 such that the vent nitrogen gases may exit the cold mass tank cavity 30 through the same bore 36 at the same time that liquid nitrogen is introduced into cavity 30 during the filling process. The preferable diameter ratio for optimal cooling and filling (least time required) is about 1.4 (bore 36 inner diameter to tubular portion 213 outer diameter). Because the bore 36 and funnel and fill tube assembly 15 permit the combined and simultaneous filling and venting of the cold mass tank cavity 30, additional ports in the cold mass tank cavity 30 are unnecessary. By minimizing the ports extending through cold mass tank 16, the unwanted heat leak into the cold mass tank 16 as well as the possibility of introducing additional complications during installation and removal of the cold mass tank 16 is significantly reduced.

The contact surface 26 of the cold mass tank 16 is preferably of the type that is "visually flat" when laid on a "marble" table with a smooth, machined finish (not polished). The exterior surface of ring 18 is preferably highly polished. In addition, reflective films (such as aluminized or silvered plastic) may be applied to the top and side of the cold mass tank for enhanced radiation reflectivity.

In order to apply a compressive force to the cold mass tank 16, compression rods 42 are retained by holding fixtures 88, each of which receives a threaded cap screw 90 which, in turn, is connected at a plug 92 to an extension tube 94. Each extension tube 94 connects to a compression rod 42 at a spring assembly 96. Each spring assembly 96 preferably includes a sleeve 98 that connects the extension tube 94 with a compression rod 42. Internal to each sleeve 98 and intermediate each extension tube 94 and compression rod 42 is a spring member 100 which may be utilized to apply a desired pressure against cold mass tank 16 and ultimately upon test specimen 12 by adjusting the length of each of the compression rods 42. The spring members 100 may be replaced by spacers (not shown) for high loading conditions or for testing of very compliant materials. The sleeves 98 may be friction fit with the extension tubes 94 as well as the compression rods 42 and set screws or cotter pins may also be utilized to retain the position of the sleeve 98 relative to the extension tube 94 and/or the compression rod 42. Each compression rod 42 and associated extension tube 94 is preferably constructed out of strong, lightweight, low thermal conductivity materials such as fiberglass reinforced epoxy composites.

The spring compression chamber 96 has been found to assist in providing for the testing of the specimens 12 that are rigid or soft or have irregular surfaces. Furthermore, the spring feature has been found to assist in providing superior thermal contact between the cold mass tank contact surface 26 and the specimen top surface 28 during the natural transitions of thermal cycling from warm to cold to warm conditions. The springs may be simply and conveniently removed and/or replaced with spacers for the performance of high compression load testing. Mechanical loading of the cold mass tank 16 against the test specimen 12 may range from zero to above 50 psig in a preferred embodiment.

One or more support guides 102 may be utilized to provide lateral support to the compression rods 42 or extension tubes 94. In the preferred embodiment there may be three compression rods 42, with one compression rod 42 obscured from view in FIG. 1 by flow-through assembly 64, with the three compression rods 42 forming a triangular shape as viewed from above. At the center of the triangle support guide 102 is an orifice 104 allowing the feed through assembly 64 and/or the tube 34 to extend through guide 102. The support guide 102 is preferably constructed of lightweight acrylic (polycarbonate). Radiation shields (aluminized of silvered plastic films) are attached to the top and bottom of each triangle support guide 102 to reflect heat away from the top surface of the cold mass tank 16.

Safety wire such as stainless steel lock wire 106 may be utilized to secure the cap screw 90 to the plug 92. The plug 92 may be joined by epoxy to an internal portion of the tube 94 or otherwise connected in a conventional manner. Weep holes 110 may be machined into the extension tube 94 to prevent pressure buildup within the extension tube 94. The holding fixtures 88 are preferably welded to the vacuum chamber lid 74 as illustrated in FIG. 1. Twisting of the compression rods 42 relative to holding fixture 88 and threaded bores 40 serves to adjust the length the various rods 42, which, in turn, adjusts the position of the cold mass assembly 16 relative to test specimen 12, thereby altering the thickness of the test specimen 12 under various test conditions. It should be noted that the thermal contraction in going from installation (at ambient temperature) to test conditions (at cryogenic temperature) is compensated for in this installation process.

Edge guard ring assembly 48 is preferably centered relative to the isothermal plate assembly 46. The guard ring assembly 48 is preferably constructed of lightweight material in continuous wraps 108 having highly reflective surfaces that function as radiation shields. Guard ring assembly 48 preferably includes two separate guard rings, an outer guard ring 49 and an inner guard ring 112. The outer guard ring 49 is preferably a specimen edge guard ring while the second guard ring 112 is preferably a cold mass edge guard ring.

Heat leak to the side and top of the cold mass tank 16 and heat leak to the edge of the test specimen 12 are minimized by four features working together: (1) reflective films on side wall and top of the cold mass tank 16; (2) isothermal plate assembly 46; (3) the use of two concentric sets of radiation shields illustrated by guard rings 49, 112; and, (4) the filling of the surrounding space with bulk insulation material 146. Because of the steps taken to control the temperature in the test apparatus 10, the affect of any heat leak on the testing process is repeatable within a narrow range from test to test and from installation to installation.

In order to evacuate the vacuum chamber 14, a vacuum port 120 may be utilized. The vacuum port 120 preferably extends into the housing wall 56 vacuum chamber 14 and provides a bore 122 in fluid communication between a vacuum pumping system (not shown) and the interior of the vacuum chamber 14. Intermediate the bore 122 and the vacuum pump is a filter assembly 124 comprising a first filter including stainless steel wool, copper wool, synthetic pad, or other appropriate material. A second layer of crushed fiberglass is located intermediate a third layer that includes an appropriate first filter material. The three filtering media extend into the bore 122 and are retained by frame wire 126. A seal assembly 128 includes an O-ring seal 130 and is designed to mate with a standard vacuum flange, but could be easily modified for other types and sizes.

The filter assembly 124 is designed to protect against both powder and particulate intrusion into the vacuum chamber 14. The load cell 44 may utilized with centering ring 132 thereabout to assist in centering the load cell 44 in a desired position. A vacuum transducer port 134 is illustrated as located on the housing wall 56 of vacuum chamber 14 to provide a convenient place to measure the internal vacuum within chamber 14.

A bake out heater 136 may be placed about a lower portion of the housing wall 56. Its use will be described in further detail below. A fiberglass insulating wrap 138 may surround the heater 136 as well as the remainder of the housing wall 56. The housing wall 56 is preferably supported by legs 140 which may be insulated by spacers 142 from a weight scale 144.

Inside the vacuum chamber 14 are insulating materials such as aerogel beads 146 or other suitable low thermal conductivity bulk-fill material which is placed about the cold mass tank 16 and the edge guards 49, 112. The vacuum chamber 14 may be reached through top ports 152, 150. The insulation 146 is preferably inserted to a level above the cold mass tank 16 and may extend to about the first support guide 102. The insulation 146 is preferably low-outgassing, reusable, minimal dusting, and hydrophobic.

Precise measurement of the thermal performance (such as the rate of heat leakage) of a test specimen 12 consisting of normal insulating material is obtainable with test apparatus 10. Of particular interest are a material's insulative properties when subjected to temperatures ranging from 77 kelvin (K) to 350 K which has been found to include cryogenic fluids, refrigeration equipment, and moderately high temperature process systems. The test apparatus 10 could be easily adapted for testing in the temperature range of about 4K to 400K or higher temperatures. Also of interest is the full range vacuum pressure conditions from high vacuum (below $1 \times 10^{-5}$ torr) to soft vacuum (approximately 1–10 torr) to no vacuum (above 760 torr). The test apparatus 10 has been designed to provide these environments as well as a specific gaseous environment in the test apparatus 10 and to evaluate the test specimen 12.

Heat leak rate measurements for a higher performance insulation systems are by nature difficult because the heat leak rate through the test specimen 12 can be small relative to the total heat leak rate to the cold mass tank 16. For cryogenic boil-off tests, obtaining proper saturation conditions of the liquid is critical and is therefore a further complication in successfully completing this type of test.

Before the present invention, it is believed that such tests were prohibitively expensive due to the specialized equipment, expertise and extended preparation time required. While insulation materials are the preferred test specimen 12, other specimens such as coated structures, biological substances, etc., may be tested. Actual use conditions including large temperatures differences (such as 300 K on one side and 77 K on the other) may be examined. Different vacuum pressure levels (from high vacuum to no vacuum) may be utilized and different gas environments may be tested as well. The gas environment, or residual gas, such as nitrogen, carbon dioxide, air, argon, helium, or other appropriate gas may be provided through ports 150 and 152 into the volume of the vacuum chamber 14. Finally, compressive mechanical loads or other combinations of all of these factors may be evaluated with the test apparatus 10 method of the present invention.

The test apparatus 10 may be utilized to measure heat leak rate through materials under conditions identical to actual use for temperature, vacuum, gaseous environment and/or mechanical loading. The preferred method of the present invention is to achieve a steady-state boil-off calorimetry using liquid nitrogen or any other suitable fluid with a normal boiling point below ambient temperature. Comparative heat leak rates and apparent thermal conductivity values may be obtained from such tests. Absolute values of the same may be calculated based on the similar testing of a known material (a standard reference material).

Test apparatus 10 has sensors including the temperature sensors 52 and 54, the vacuum transducer 148, the load cell 44, the weight scale 144, and the mass flow meter 86, which are preferably all connected to a processor assembly 200 as shown in block diagram in FIG. 1 which provides real-time data display and recording capability. The processor assembly 200 may take the form of a PC-based data acquisition system. In addition to utilizing a plurality of sensors for monitoring the thermal characteristics of the test specimen 12, the test apparatus 10 may include a control system for conducting and initiating various tests. The data and control system can be made semi-automated for conducting test and evaluation of large numbers of specimens or, for example, a production quality control application.

The test apparatus 10 is relatively quick in performance of the actual testing procedure as well as allowing for quick specimen change out. Apparatus 10 is mobile as well as portable and can be adapted to specimen of significantly differing size and thickness. The thickness of a test specimen 12 is easily adjusted by merely adjusting screws 90 to increase or decrease pressure against cold mass tank 16 that, in turn, varies the pressure against the test specimen 12.

Although boil-off is the preferred method of utilizing test apparatus 10, dynamic (transient heat flux) methods of testing may also be utilized with test apparatus 10. The present invention is believed to be more efficient to set up and operate than known prior art assemblies and is useful for cryogenic refrigeration and low temperature testing. It is more economical due to the relatively small amounts of fluid consumed, quick change out of test specimens, and no user intervention required during steady-state operation. The test apparatus 10 can be set up and operated for a very minimal user intervention.

The procedure for utilizing test apparatus 10 is considered to be straightforward. With vacuum chamber 14 initially empty, a test specimen 12 is placed on copper disk 50 located on the bottom 24 of the vacuum chamber 14. Cold mass tank 16 is disposed within vacuum chamber 14 so that the contact surface 26 contacts the first surface 28 of the test specimen 12. The edge guard rings 49, 50 are placed about the cold mass tank 16. The position of cold mass tank 16 relative to test specimen 12 can be adjusted by merely adjusting the position of the compression rods 42 relative to the bosses 38 and holding fixtures 88. It is important to remember that as the temperature changes in the vacuum chamber 14, some of the components may shrink or expand with the change in temperature. Spring assemblies 100 are included to provide compliance and ensure good thermal contact of both sides of the test specimen 12 during all phases of the test operations. Insulation material 146 is positioned to fill the vacuum chamber 14 up to a desired level, preferably extending beyond cold mass tank 16 into vacuum chamber 14. A desired vacuum pressure level is then produced within vacuum chamber 14. The cold mass tank 16 is then cooled and filled with liquid nitrogen or other appropriate boil-off cryogenic fluid. Once the desired steady state conditions are achieved, the comparative heat flux or k-value can be calculated. The final steady-state measurement value is typically taken at the last moment before the cold mass tank 16 becomes empty. This ensures repeatability and strict accuracy of the thermodynamic condition of the boil-off liquid.

The comparative apparent thermal conductivity (k-value) is determined by using the Fourier heat conduction equation:

$$Q = \text{Heat Transfer Rate} = \frac{k(\text{Area})(\Delta T)}{\Delta x} \quad [W] = [J/s]$$

where, k=apparent thermal conductivity (k-value) [mW/m-K]

$\Delta T$=temperature difference between the warm boundary surface and the cold boundary surface [K]

$\Delta x$=thickness of the test specimen [m]

The equation is modified for use of the circular heat transfer surface area to:

$$Q = \frac{\pi \, h \, d^2 \Delta T}{4 \Delta x}$$

where: d=effective diameter of the cold mass tank [m]

Remember, $Q = M \times (H_{fg})$ [W]=[J/s]

$H_{fg}$=Heat of vaporization of the boil-off liquid [J/g]

M=Mass flow rate of the boil-off gas [g/s]

The mass flow rate (or boil off flow rate) is typically measured by two ways: flow meter and weight scale. The entire test apparatus 10 is typically placed on a weight scale. Flow computed from the weight decay rate is used to check the flow indicated by the flow meter. The weight scale is also helpful in the filling process of cold mass tank 16 and other test operations.

While the steady-state boil off method is particularly attractive for determining thermal characteristics for test specimens 12 utilized in cryogenic or low temperature systems, transient heat flux testing may also be performed. The warm and cold boundary conditions are set and stabilized as desired. The boil-off liquid is quickly admitted to the cold mass tank 16 by the appropriate filling funnel and tube assembly 15 formed in accordance with the present invention. The resulting time-temperature response is recorded by the data acquisition system. For example, the freezing rate and temperature profile of a biological tissue can be studied by using temperature sensors embedded within the test specimen.

This test apparatus 10 is constructed as a comparative test device in the preferred embodiment. A test specimen 12 of known characteristics may also be tested to determine parasitic heat leak rate so that an absolute k-value may be calculated from the comparative k-value.

While the preferred embodiment relates to use with cryogenic fluids, other fluids, with normal boiling points below room temperature may also utilize a similar test apparatus 10 within the scope of the present invention. The evaluation of cryogenic insulation typically includes high performance materials that have apparent thermal conductivities below 0.1 mW/m-K. There is no higher limit k-value for the preferred embodiment. The test apparatus has a sufficiently high sensitivity such that thermal systems with k-values in the range of 0.01 mW/m-K to 100 mW/m-K can be effectively tested.

Numerous alternations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

We claim:

1. A test apparatus for evaluating thermal properties of a test specimen, comprising:

a chamber;

a cold mass tank located within the chamber, said cold mass tank having a cavity adaptable for receiving a quantity of liquid, said cold mass tank also having a contact surface adaptable for contacting a first side of the test specimen positioned within said chamber, with the chamber having a contact surface adaptable for contacting a second, oppositely disposed side of the test specimen;

a quantity of bulk insulation material surrounding the cold mass tank;

a passageway assembly extending through the chamber, bulk insulation material and into the cold mass tank for introducing a quantity of liquid fluid into the cold mass tank and subsequently expelling boiled-off gas from the cold sass tank cavity, whereby the thermal performance of the test specimen is determined; and a plurality of spaced-apart and parallel extending compression rod assemblies located within the chamber, each compression rod assembly comprising an elongated spring rod and an elongated extension tube having confronting end portions extending within a connecting sleeve and engaging opposite ends of a compression spring, wherein each compression rod assembly is disposed such that one end portion engages the chamber and an opposite end portion engages the cold mass tank for pressing the cold mass tank against the specimen with a predetermined and controllable level of force.

2. The test apparatus of claim 1, further including a sensor assembly electronically connected to a processor capable of collecting sensor data measuring properties indicative of thermal properties of the test specimen.

3. The test apparatus of claim 2, wherein the sensor assembly includes at least one first temperature sensor in contact with the first side of the test specimen and at least one second temperature sensor in contact with the second side of the test specimen.

4. The test apparatus of claim 2, further comprising a processor in communication with the sensor assembly for calculating at least one thermal characteristic of the test specimen.

5. The test apparatus of claim 2, wherein the sensor assembly further comprises at least one sensor in fluid communication with the liquid fluid in the cold mass tank and in electronic connection with the processor.

6. The test apparatus of claim 1, further comprising a heater disposed to provide heat to the contact surface of the chamber, whereby heat travels from the chamber, through the test specimen and serves to heat the liquid located in the cold mass tank.

7. The test apparatus of claim 1, wherein the chamber is a vacuum chamber having an air-tight barrier adaptable for maintaining a chamber pressure between about 0.01 and 1,000,000 millitorr.

8. The test apparatus of claim 1, further comprising a vacuum port equipped with a filter assembly having a base with an O-ring forming a seal intermediate the vacuum port and the base, and filter media extending from the base having a first layer of fine filter media and a second layer of coarse filter media, wherein fluid communication through the base into the chamber requires passage through at least a portion of the filter media.

9. The test apparatus of claim 1, further comprising at least one edge guard positioned within the chamber, extending through a portion of the bulk insulation material and at least partially encircling the cold mass tank.

10. The test apparatus of claim 1, wherein the passageway assembly comprises a single feed-through bore extending through aligned openings in the chamber, the bulk insulation material and the cold mass tank cavity for providing the only passageway adaptable for introducing liquid fluid into the cold mass cavity and for venting boil-off gas exiting from the cold mass cavity.

11. The test apparatus of claim 1, wherein the liquid fluid is a cryogenic liquid.

12. The test apparatus of claim 1, further comprising a load cell located between the test specimen and wall of the chamber for measuring the pressure imposed by the at least one compression rod assembly against the test specimen.

13. The test apparatus of claim 1, wherein the bulk insulations material comprises a hydrophobic material enclosing the cold mass tank and contacting an edge portion of the test specimen.

14. The test apparatus of claim 13, wherein in the bulk insulation material is low outgassing, reusable and creates minimal dusting.

15. A method of measuring the thermal characteristic of a test specimen, comprising the following steps of:

(a) placing a test specimen having first and second oppositely disposed surfaces within a vacuum chamber;

(b) positioning a cold mass tank having a cavity within the chamber so that a contact surface boundary of the cold mass tank cavity engages the second surface of the test specimen;

(c) compressing a plurality of spaced-apart and parallel extending compression rod assemblies between the chamber and the cold mass tank with each compression rod assembly comprising a compression rod and an extension tube having confronting ends extending within a connecting sleeve and engaging opposite ends of a spring for pressing the cold mass tank against the test specimen with a predetermined and controllable level of force;

(d) surrounding the cold mass tank with a quantity of bulk insulation material;

(e) heating the first surface of the test specimen;

(e) filling the cold mass tank cavity with a liquid fluid;

(f) completely venting all boiled-off gases from the cold mass tank cavity; and (h) measuring the steady state heat transfer through the test specimen between the first and second surfaces.

16. The method of claim 15, further comprising the step of measuring a value of the liquid fluid in the cold mass tank and utilizing the value to provide the insulation value of the test specimen.

17. The method of claim 15, further comprising the step of drawing and measuring a cold vacuum pressure in the vacuum chamber.

18. The method of claim 15, further comprising the step of applying a specific gaseous environment in the chamber.

19. The method of claim 15, including the further step of filling the cold mass tank cavity with a cryogenic liquid.

20. The method of claim 15, including the further step of filling the cold mass tank with liquid nitrogen.

21. The method of claim 15, including the further step of maintaining the cold mass tank contact surface at a steady state temperature of approximately 80 K.

22. The method of claim 15, including the further step of applying a vacuum to the chamber of approximately $1 \times 10^{-5}$ torr.

* * * * *